United States Patent [19]

Ghebre-Sellassie et al.

[11] Patent Number: 4,786,508
[45] Date of Patent: Nov. 22, 1988

[54] COATED DOSAGE FORMS

[75] Inventors: Isaac Ghebre-Sellassie, Stanhope; Robert Gordon, Dover; Maryann Mench, Wharton; Russell U. Nesbitt, Jr., Somerville; Mary E. Trapold, Morris Plains, all of N.J.

[73] Assignee: Warner-Lambert Company, Morris Plains, N.J.

[21] Appl. No.: 869,504

[22] Filed: May 30, 1986

[51] Int. Cl.⁴ .......................... A61K 9/32; A61K 9/28
[52] U.S. Cl. .................................... 424/482; 424/497
[58] Field of Search ................................ 424/482, 497

[56] References Cited

U.S. PATENT DOCUMENTS 4,101,651 7/1978 Kobayashi et al. .................. 424/35

OTHER PUBLICATIONS

Elan Corp. GA. 101:235590k (1984) of Belg. 899464, Aug. 16, 1984.

Elan Corp. GA. 101:235591m (1984) of Belg. 899293, Aug. 16, 1984.

"Eudragit-Acrylic Resins at One Glance", Rohm Pharma GmbH

"The Application and Processing of Acrylic Coatings in Form of Aqueous Dispersions Compared with Organic Solutions", Klaus Lehmann, Acta Pharm. Fenn. 91, 225-238 (1982).

"Coating of Tablets and Small Particles with Acrylic Resins by Fluid Bed Technology", K. Lehmann and D. Dreher, Int. J. Pharm. Tech & Prod Mfr.

Primary Examiner—Shep K. Rose
Attorney, Agent, or Firm—Howard Olevsky; Ronald A. Daignault

[57] ABSTRACT

Aqueous solutions of certain cationic (meth)acrylic ester copolymers can be used to coat dosage forms to taste- and odor-mask bio-active agents therein. Pellets are highly preferred dosage forms.

5 Claims, No Drawings

COATED DOSAGE FORMS

BACKGROUND

The oral administration of foul-tasting and smelling pharmaceutical and/or other bioactive agents to youngsters and to older individuals who must take them on a regular basis is frought with compliance problems. Many attempts have been made to mask the odor and flavor of such agents and, thus, eliminate these problems.

THE INVENTION

It has been discovered that the taste and/or odor associated with some bioactive agents, e.g., guaifenisan, procainamide, and the like can be overcome by coating the oral dosage form with a novel composition which prevents the ingester's perception of the disagreeable odor and/or flavor.

The compositions contain cationic (meth) acrylic polymers and can be applied, via conventional techniques, to a variety of orally administered dosage forms, e.g., powders, pellets, and tablets.

One preferred embodiment of the invention involves the use of Eudragit E-100 with dilute acetic acid, (pH>2.0), a plasticizer and/or a neutral polymer, and talc as an optional separating agent, in a liquid coating formulation. This formulation is useful for coating pellets containing drugs or other ingestibles.

ADVANTAGES OF THE INVENTION

Besides its obvious advantage as a means of substantially reducing non-compliance among animals or individuals taking oral medication or other beneficial ingestible substance, the invention has renewed advantages over prior art coatings and dosage forms made therewith.

The subject coatings are generally aqueous. Thus, the use of solvents and their inherent environmental hazards, is eliminated. Additionally, some solvents may remain as a residue in the dosage form and can cause unwanted side effects after administration.

The coatings of the invention yield saliva-resistant coverings on the dosage forms to which they are applied. Thus, unless the person or animal ingesting the pill or other treated dosage form bites into it, there will lbe little or no sensation of taste, smell or mouth-feel. This is particularly true of pellets and powders which, is sufficiently small, can be swallowed virtually unperceived.

In addition, small pellets coated with the subject compositions can be easily ingested by individuals who may have difficulty swallowing, e.g., the elderly, small children, and animals.

Furthermore, depending upon the character of the encapsulating substance, when pellets are made using the invention, they can be employed to produce sustained release effects. Thus if certain enteric materials, e.g., cellulose derivatives, are employed as encapsulants, the active ingredients contained in the pellets will be protected from gastric substances in the body for a limited time, with the result that such ingredients get into the blood stream gradually, i.e., over a longer interval of time.

Lastly, stability and packaging advantages result from the use of the invention. The ingestibles put into the pellets and other dosage forms of the invention may be reactive or unstable in the presence of sweeteners, odorants and other additives conventionally employed in the formulation of tablets and liquid dosage forms.

Packaging and handling problems are eliminated because the inventive dosage forms can be made so small that breakage is not a significant consideration. Also, pellets, being solids, need not be packaged as tightly as liquids.

Other aspects and advantages of the invention will become apparent from a consideration of the following description of the invention.

DESCRIPTION OF THE INVENTION

The invention deals with:
I. Coating compositions; and
II. Dosage forms coated with the compositions of I; and
III. Unit and multi-dose packages containing supplies of dosage forms coated with the composition of I.

Coating Compositions

The coating compositions of the invention are generally liquid formulations. While they may be applied, using suitable apparatus, in the dry or fused state, it is generally preferred, for ease of handling, that they be applied to the dosage form to be treated in a liquid state.

The coatings are preferably employed as aqueous formulations. While the essential polymeric ingredient is preferably dissolved completely in the aqueous medium, it may be at least partially dispersed therein. Co-solvents, if present, will generally be used in minor amounts, i.e., about 25% of total solvent or less. When used, such co-solvents will be of polar character and be compatible with the polymeric component, e.g., the (meth) acrylic copolymer, employed.

The compositions of the invention contain as essential ingredients an amino group containing or cationic polymeric component and an acid component. The use of processing aids, such as separating agents, is optional.

The polymeric component contains at least one copolymer of a methacrylic ester and a dimethyl aminoethyl (meth) acrylate. By employing "meth" as a prefix in parentheses, Applicants intend to indicate that molecules derived from one or both of acrylic and methacrylic species are operable. Thus, the copolymer may be derived from dimethylaminoethyl methacrylate and methyl acrylate. Other conventional comonomers may be present in the copolymers as long as they do not detract from the copolymer's usefulness in the present coating system.

Generally, the molecular weight of the (meth) acrylic polymers will be about 100,000 to about 200,000. Additionally, the copolymers are usually cationic molecules. One preferred copolymer is "Eudragit E 100" from Rhome Pharma. It is an acrylic resin based on dimethylaminoethyl methacrylic acid esters, having a molecular weight of about 100,000 to about 150,000. A molecular weight of about 150,000 is preferred. It is preferred that the cationic polymer employed be soluble in gastric fluid up to a pH of about 5.

Mixtures of several of these copolymers, as well as combinations of these with other polymeric materials, are operable. It is generally preferred to use mixtures containing Eudragit E 100 with Eudragit E 30D or other suitable neutral polymer as a component of the instant formulations.

The acidic component of the inventive composition acts as a solubilizer for the polymer and will generally be at least one dilute mineral acid or organic acid or acid-functional material having a pKa of about 2 to about 6. Preferred acids are hydrochloric, nitric, sulfuric, acetic, citric, oxalic, propionic and the like. Mixtures are operable.

Generally, the pH of the combination of polymeric and acidic components will be from about 1 to about 6, preferably about 2 to about 4.

The use of one or more colorants, perfumes, processing aids, and other excipients conventionally used in the preparation of dosage forms is contemplated.

The processing aids contemplated for use in the subject formulations include separating agents, plasticizers, stabilizers and the like.

By "separating agents", applicants means antitackiness agents. Useful agents include hydroxy propyl methyl cellulose kaolin, talc, magnesium trisilicate, silicon-dioxide, calcium carbonate and the like. Talc is a preferred agent. Mixtures are operable.

The physical form of the dosage form to be treated is not critical. Generally, the bioactive agent to be treated or contacted with the coating of the invention will be a solid or semi-solid material. Its solid or semi-solid state may be achieved via the use of solid and/or liquid carriers or other suitable materials.

When solids are treated, they are usually powders, pellets, granules, or tablets. Physical dimensions are generally dictated by the quantity of bio-active agent present in the dosage and/or other consideration such as ease of ingestion and the limitations of the machinery employed to apply the compositions to the substrate, e.g., the tablet.

The bio-active ingredients to be included in the dosage form of the invention can be of various types. Generally, any drug, vitamin, mineral, hormone, etc., which is beneficial to the health of the patient or other subject to whom it is administered can be used. Mixtures of various types of bioactives are operable.

Useful drugs include analgesics antihistamines, antibiotics, antiarrhythmics cough suppressants, decongestants, alkaloids, antihypertensives. Mixtures can be used.

The advantages of the invention are fully realized when the bio-active agent comprises one or more substances which have a disagreeable odor and/or taste. Well-known agents include acetaminophen, phenytoin, diphenhydramine hydrochloride, quiafenesin, N-acetylprocainamide hydrochloride and the like. Drug bases and their salts are operable. Mixtures are operable.

The nature of the drug or other bio-active bio-active ingredient is not critical. Unlike the interactive system described in U.S. Pat. No. 3,608,068, applicants' drug or bio-active substrates need not have any chemical affinity or interaction with either the acid or polymeric component. Thus applicants' coatings are true coatings in that no interaction or reaction between the polymer-/acid composition and the drug is expected.

The apparatus employed to treat substrates with the instant coating materials is not critical. Generally, any device will suffice as long as it can effectively coat the medicament or other ingestible agent with a sufficient quantity of the coating to hide the bad taste, smell, or mouthfeel of the active ingredient. One preferred type of coating device is a fluid bed apparatus.

The treated or coated dosage forms made in accordance with the invention will have final compositions as shown in the following table:

TABLE I

| Ingredient | Final Composition Ranges | |
| --- | --- | --- |
| | Broad | Preferred |
| Cationic Polymer | 1–25 gm | 4–10 gm |
| Acid | 50–150 ml | 80–120 ml |
| Plasticizer/neutral polymer | 2–10 gm | 4–8 gm |
| Excipients | Balance | Balance |

Pellets

One preferred embodiment of the invention deals with pellets having an average diameter of about 0.35 mm to about 1.00 mm, which, which pellets contain at least one ingestible substance inside at least one layer of a coating material described above.

Size is an important characteristic of the pellets of the invention. Generally, the coated or encapsulated pellets will have an average diameter of about 0.35 mm to about 1.00 mm, with those of about 0.4 mm to about 0.8 mm, preferred and those of about 0.5 mm to about 0.6 mm highly preferred. These diameters are the total diameters of the pellets, re: it is based on the size of the coated material.

The shape of the pellets is not important. However, for ease of swallowing generally spherical shapes are preferred.

The coating or encapsulating materials described above are generally acid-soluble materials in nature. Thus, the true odor or taste of the medicament or drug encapsulated is not picked up by the taste buds and/or olfactory sensors. It is not until the pellets reach the acidic environment of the stomach that the coating dissolves, releasing all or part ofthe ingestible material inside. Mixtures of coating or encapsulating materials are operable.

The absorbable, i.e. active, component of the ingestible pellets of the invention can be any substance which is generally beneficial to the patient to whom it is being administered—i.e., any material having nutrient and/or therapeutic value. While pleasant-tasting and pleasant-smelling ingestible substances can be put into the pellets, candidates for use as the active component herein are generally those materials having a bitter or sour taste and/or a foul smell. Acetaminophen, potassium chloride, guaifenisan, potassium chloride, vitamins, such as vitamin B complex and vitamin C, and minerals, e.g., iron are among the bitter-tasting drugs contemplated. Mixtures are operable.

The coating material used to cover or encapsulate the active or ingestible component is one whose solubility characteristics make it practically insoluble in the mouth, but readily soluble in an acid environment, such as in the gastric juices of the digestive tract, particularly the stomach.

For handling and packaging purposes, it is preferred that the coating substance be polymeric. However, other types of coating materials can be substituted for all or part of the polymeric coating.

The polymeric coating materials to be used in the invention are generally acid-soluble resins. It is preferred that they be soluble at pH 5 and below. Suitable resins include synthetic acrylic resins and natural polymeric derivatives meeting these solubility requirements. Preferred resins include cellulose derivatives and addition polymers derived from reactants containing unsaturated acid, salt, and/or ester moieties. The Eudragit polymers discussed above are highly preferred. Carriers, fillers and various processing aids can be used.

The relative amounts of active component and coating or encapsulating material in the pellets can vary within wide limits. Generally, the pellets will contain about 55 to about 80 weight percent, preferably about 65 to about 80 weight percent, active or ingestible material, e.g., drug; and about 2 to about 80, preferably, about 8 to about 20, and most preferably about 10 to about 15 weight percent, coating material. These weight percentages are generally based on total pellet weight. The manufacturing process used will have a bearing on final weight percentages.

The production of the pellets can be carried out using conventional pelletizing devices. Preferred methods of producing pellets include:

a. coating non-pariel seeds with a binder and drug powder on a granulator, e.g. a C.F. Granulator, manufactured by Freund ® e.g., the model CF 360; and b. pelletizing on an extruder, e.g. a Fuji Paudal ® Model EXDS-60.

The binders used in the pelletizing operation may be any of those conventionally employed. Suitable binders include polyvinylpyrrolidone, hydroxypropyl cellulose, methyl cellulose, hydroxyethyl cellulose, ethylcellulose, sodium carboxymethylcellulose, gelatin, starch, and the like. Mixtures are operable.

The pellets of active substance are then coated, using conventional coating or encapsulating techniques, with one or more of the coating materials discussed above.

Suitable coating methods include fluidized bed and centrifugal fluidized bed methods and the like.

Several packaging concepts are useful for handling and distributing the pellets of the invention.

The pellets can be put into unit dosage containers such as pouches or bags. It would then be a simple matter of mixing the contents of the package, i.e., a premeasured supply or dosage of the pellets, with a food or other consumable material that is convenient and/or palatable to the patient.

Another packaging concept would involve the use of a large bulk of pellets in a suitable container, e.g., a jar, box, bottle or the like. A suitable measuring dispenser, e.g., a scoop, spoon or other suitable device could then be used to remove usable quantities, e.g., one or more dosages, of the pellets.

Yet another embodiment would involve a container whose lid or closure, e.g., a snap- or screw-on top could also serve as a measuring dispenser. A bulk package with a calibrated cap which serves as a dispenser is contemplated.

While the use of the subject pellets in capsules is envisioned, capsules are not a principal packaging vehicle. It should be recognized, however, that the subject pellets can be packaged inside capsules which are adapted so that they can be easily opened. Once the capsules are opened, the pellets therein can be removed, and, preferably mixed with food, before swallowing.

Other packaging schemes can be used instead of, or in combination with, those discussed above.

While particular attention has been given to the use of the coatings of the invention in the production of easily swallowed pellets, applicants do not intend to limit their invention thereto. The coatings can be used on a variety of dosage forms to be administered orally or parenterally.

The invention can be better understood by reference to the following example(s).

EXAMPLES

EXAMPLE 1

Eudragit E-100 is dissolved in 0.1N hydrochloric acid to generate a 4% polymeric solution. The solution was then mixed thoroughly with a known quantity of Eudragit E 30 D dispersion to produce the required amount of resin in the final coating material. Finally, a suspension of talc in 0.1N hydrochloric acid was added to the mixture to make up the coating formulation.

EXAMPLES 2 AND 3

Examples of Eudragit E-100 formulations include:

| (A) | 2.000 kg Eudragit E 30 D |
|     | 0.100 kg Eudragit E-100 |
|     | 0.100 kg Talc |
|     | 5.800 kg 0.1 N Hydrochloric Acid |
| (B) | 2.000 kg Eudragit E 30D |
|     | 0.100 kg Eudragit E-100 |
|     | 0.100 kg Talc |
|     | 3.130 kg 0.1 N Hydrochloric Acid |

Guaifenisan and N-acetylprocainamide hydrochloride were coated in the Glatt GPCG-5 using various Eudragit E-100 formulations. The organoleptic properties of these drugs were completely masked without having an adverse effect on dissolution.

Eudragit E 30 D can be replaced by a suitable plasticizer if desired. Alternatively, the quantities of Eudragit E 100 can be increased tenfold or more without affecting film integrity.

EXAMPLE 4

A prototype pellet useful as an oral pediatric form for administering acetaminophen has been produced. A dosage guideline of 10–15 mg/kg of body weight four to five times daily can be used or a suitable value from the following table can be employed.

| PEDIATRIC DOSAGES OF ACETAMINOPHEN | |
|---|---|
| Age (Yrs) | Dosage (mg) |
| 2–4 | 160 |
| 4–6 | 240 |
| 6–9 | 320 |
| 9–11 | 400 |
| 11–12 | 480 |

Acetaminophen pellets would also be beneficial for noncompliant geriatric patients as well as those who have difficulty swallowing solid dosage forms. If recent evidence suggesting acetaminophen's effectiveness as an anti-inflammatory and antiarthritic proves true, it will become more useful to the elderly, especially considering its lack of gastric upset. The usual adult dose is 325–650 mg every four hours, so a unit dose of 325 mg is operable for geriatric patients.

Typical formulations for acetaminophen pellets would contain:

| Formulation | Eudragit E-100 (gms) | Acetic Acid (ml)* | Hydroxypropyl Methylcellulose (ml)+ |
|---|---|---|---|
| A. Preferred | 20.0 | 250 | 250 |

-continued

| Formulation | Eudragit E-100 (gms) | Acetic Acid (ml)* | Hydroxypropyl Methylcellulose (ml)+ |
|---|---|---|---|
| B. Alternate | 18.6 | 300 | 0 |

*0.2 N acetic acid solution.
+2% aqueous hydroyxpropyl methylcellulose solution.

Reasonable variations, such as those which would occur to a skilled artisan, can be made herein without departing from the scope of the invention.

We claim:

1. A pharmaceutical substance in oral dosage form having a saliva resistant-acid soluble coating, said coating comprising:
   (a) a polymeric component containing a cationic copolymer which contains residues of (meth)acrylic esters and dimethyl aminoethyl (meth)acrylate, said coating deposited from an aqueous acidic solution having a pH between 1 and 6.

2. The coating of claim 1 wherein the coating comprises at least one processing aid and a plasticizer or neutral polymer.

3. The substance of claim 1 wherein the processing aid is selected from the group consisting of talc, kaolin and magnesium trisilicate, silicon dioxide and calcium carbonate.

4. A pharmaceutical substance wherein the oral dosage form is a pellet having an average diameter of 0.35 mm to 1.00 mm.

5. A dosage form wherein the pharmaceutical substance is acetaminophen.

* * * * *